US011357490B2

(12) United States Patent
Gasser

(10) Patent No.: US 11,357,490 B2
(45) Date of Patent: Jun. 14, 2022

(54) DISTRACTOR DEVICE AND METHOD

(71) Applicant: SWISS MEDICAL INSTRUMENTS AG, Wollerau (CH)

(72) Inventor: André Gasser, Luterbach (CH)

(73) Assignee: SWISS MEDICAL INSTRUMENTS AG, Wollerau (CH)

( * ) Notice: Subject to any disclaimer, the term of this patent is extended or adjusted under 35 U.S.C. 154(b) by 226 days.

(21) Appl. No.: 15/763,066

(22) PCT Filed: Dec. 4, 2015

(86) PCT No.: PCT/IB2015/059354
§ 371 (c)(1),
(2) Date: Mar. 23, 2018

(87) PCT Pub. No.: WO2017/051226
PCT Pub. Date: Mar. 30, 2017

(65) Prior Publication Data
US 2018/0271507 A1    Sep. 27, 2018

(30) Foreign Application Priority Data

Sep. 24, 2015 (EP) .................................... 15186775

(51) Int. Cl.
*A61B 17/02* (2006.01)
*A61B 17/86* (2006.01)
(Continued)

(52) U.S. Cl.
CPC ........ *A61B 17/025* (2013.01); *A61B 17/0206* (2013.01); *A61B 17/6483* (2013.01);
(Continued)

(58) Field of Classification Search
CPC .............. A61B 17/025; A61B 17/0206; A61B 17/6475; A61B 17/683; A61B 17/60
See application file for complete search history.

(56) References Cited

U.S. PATENT DOCUMENTS 1,920,821 A * 8/1933 Wassenaar ......... A61B 17/6408
606/86 R
3,997,138 A * 12/1976 Crock ................ A61B 17/7001
248/67.5
(Continued)

FOREIGN PATENT DOCUMENTS

EP          0 499 037 A2   8/1992
EP            499037    *  8/1992  ........... A61B 17/025
(Continued)

*Primary Examiner* — Christian A Sevilla
(74) *Attorney, Agent, or Firm* — Maschoff Brennan

(57) ABSTRACT

A distractor device includes a longitudinal guiding element and a longitudinal driving element, such as a threaded rod, which may be arranged substantially parallel to the guiding element such that the threaded rod may rotate about a rotation axis substantially parallel to the longitudinal axis of the guiding element. First and second distractor arms are arranged extending along first and second lateral axes from the guiding element. The first and second lateral axes are substantially orthogonal to the longitudinal axis of the guiding element. The first and second distractor arms are captively displaceable along the guiding element, such that the first and second distractor arms are displaceable away from each other by rotating the threaded rod in a first rotational direction, and towards each other by rotating the threaded rod in a second rotational direction, the second rotational direction being opposite to the first rotational direction.

15 Claims, 6 Drawing Sheets

(51) Int. Cl.
    *A61B 17/66*     (2006.01)
    *A61B 17/64*     (2006.01)
    *A61B 90/00*     (2016.01)
    *A61B 17/68*     (2006.01)

(52) U.S. Cl.
    CPC .............. *A61B 17/66* (2013.01); *A61B 17/86* (2013.01); *A61B 2017/0275* (2013.01); *A61B 2017/681* (2013.01); *A61B 2090/0811* (2016.02)

(56) References Cited

U.S. PATENT DOCUMENTS

| | | |
|---|---|---|
| 2007/0225704 A1 | 9/2007 | Ziran et al. |
| 2008/0077155 A1* | 3/2008 | Diederich ............ A61B 17/708 606/105 |
| 2010/0104999 A1 | 4/2010 | Bulloch et al. |
| 2010/0222644 A1 | 9/2010 | Sebastian et al. |
| 2010/0222784 A1 | 9/2010 | Schwab et al. |
| 2014/0257312 A1 | 9/2014 | Solitario, Jr. et al. |

FOREIGN PATENT DOCUMENTS

| | | | |
|---|---|---|---|
| WO | 90/02527 A1 | 3/1990 | |
| WO | WO9002527 * | 3/1990 | ............ A61B 17/025 |

* cited by examiner

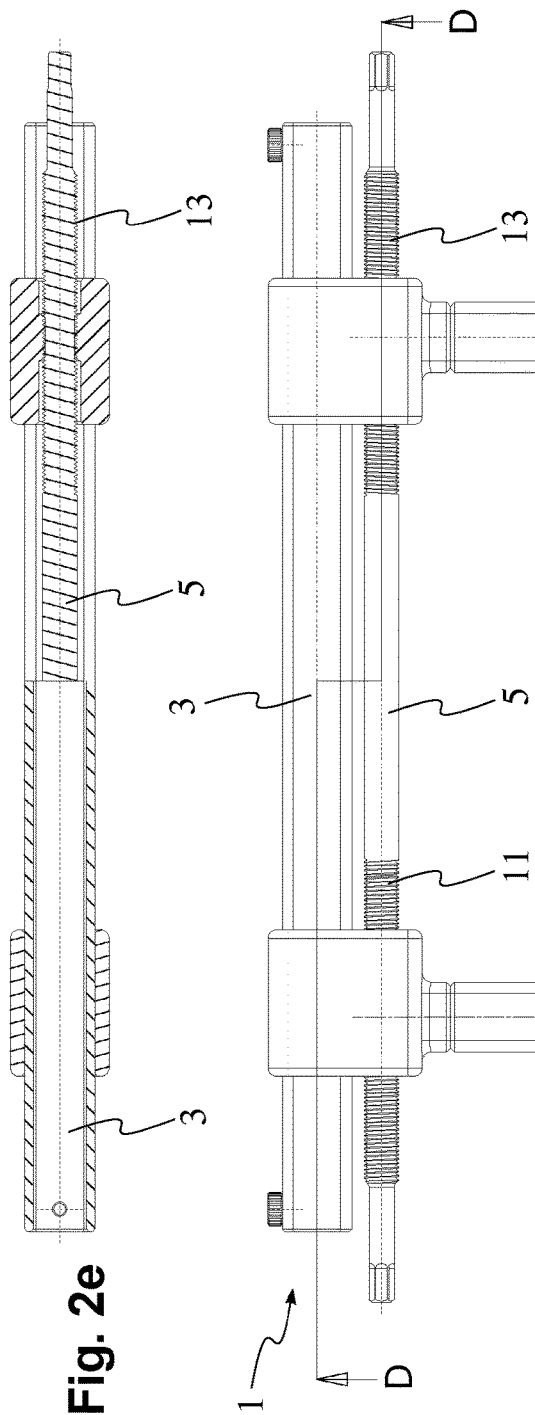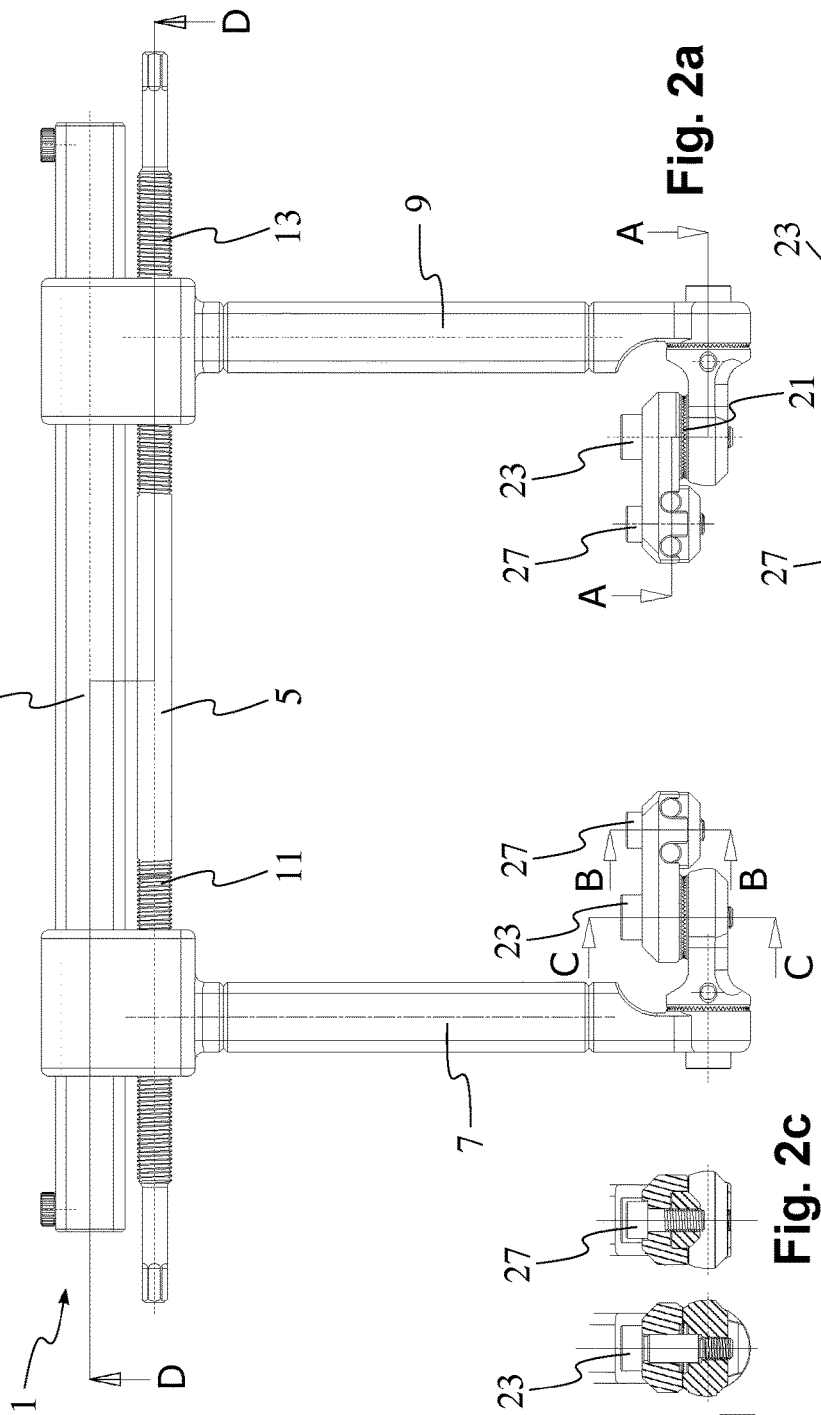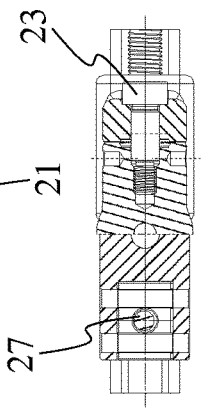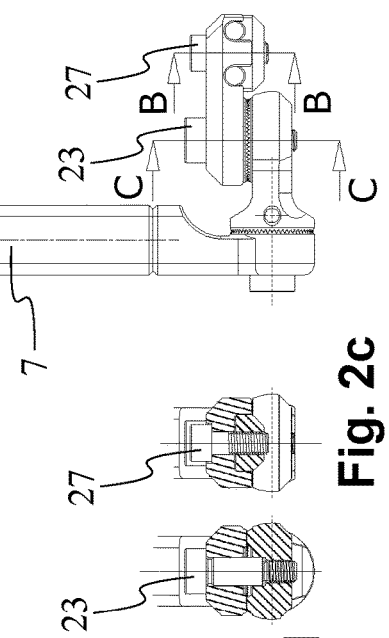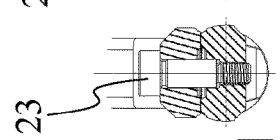

DISTRACTOR DEVICE AND METHOD

TECHNICAL FIELD

The present invention relates to distraction devices and methods for joint distraction, for example for surgical procedures such as arthroplasty or arthroscopy. In particular, but not exclusively, the invention relates to methods and devices which can be used for hip distraction.

BACKGROUND OF THE INVENTION

Hip pain in young adults is often characterized by non-specific symptoms, normal imaging studies and vague findings from history and physical examination. As such, identifying the source and mechanism of the pain can be difficult. At the same time, treatment needs to be specific because its effects will be experienced longer in this population. In complex arthroscopic reconstructive surgery, for conditions such as femoroacetabular impingement in young adults, relatively long traction times are necessary. Traction times longer than 90 minutes on a traction table can provoke severe neurological and perineal skin lesions. The most frequent neurological lesions reported are pudendal nerve lesions with clinical impotence due to the compression of the nerve on the perineal post on traction tables. Sciatic and femoral nerves are also at risk due to their overstretching during longer periods of time. Such reconstructive procedures have hitherto been seen as time consuming, have a steep learning curve and can provoke complications. The available distraction equipment is cumbersome, time-consuming to set up and adjust, and complex to manufacture.

There is thus a need for a robust invasive distraction device which avoids the need for a traction table, which is quick to set up and adjust, which can be quickly learned, and/or which is nevertheless simple in construction and manufacture.

SUMMARY OF THE INVENTION

According to a first aspect of the invention, there is provided a distractor device as recited in claim 1.

By arranging the distractor arms so that they can be forced apart by a single operation (the rotation of the driving element, which may be a threaded rod), the operation of the device can be greatly simplified. By separating the arm-guiding function, performed by the guiding element, from the drive function, performed by the driving element, both the guiding element and the driving element can be constructed more simply and more robustly.

According to a second aspect of the invention, there is provided a method of operating the distractor device as recited in claim 15.

Other aspects of the invention are recited in the dependent claims attached hereto.

BRIEF DESCRIPTION OF THE DRAWINGS

Other features and advantages of the invention will become apparent from the following description of a non-limiting exemplary embodiment, with reference to the appended drawings, in which:

FIG. 2a is a top view of the distractor device of FIG. 1;

FIG. 2b is a cross-sectional view of a head element of the distractor device taken along line A-A in FIG. 2a;

FIG. 2c is a cross-sectional view of the head element of the distractor device taken along line B-B in FIG. 2a;

FIG. 2d is a cross-sectional view of the head element of the distractor device taken along line C-C in FIG. 2a;

FIG. 2e is a cross-sectional view of the guiding element and driving element taken along line D-D in FIG. 2a;

DETAILED DESCRIPTION OF AN EMBODIMENT OF THE INVENTION

Figure 1:
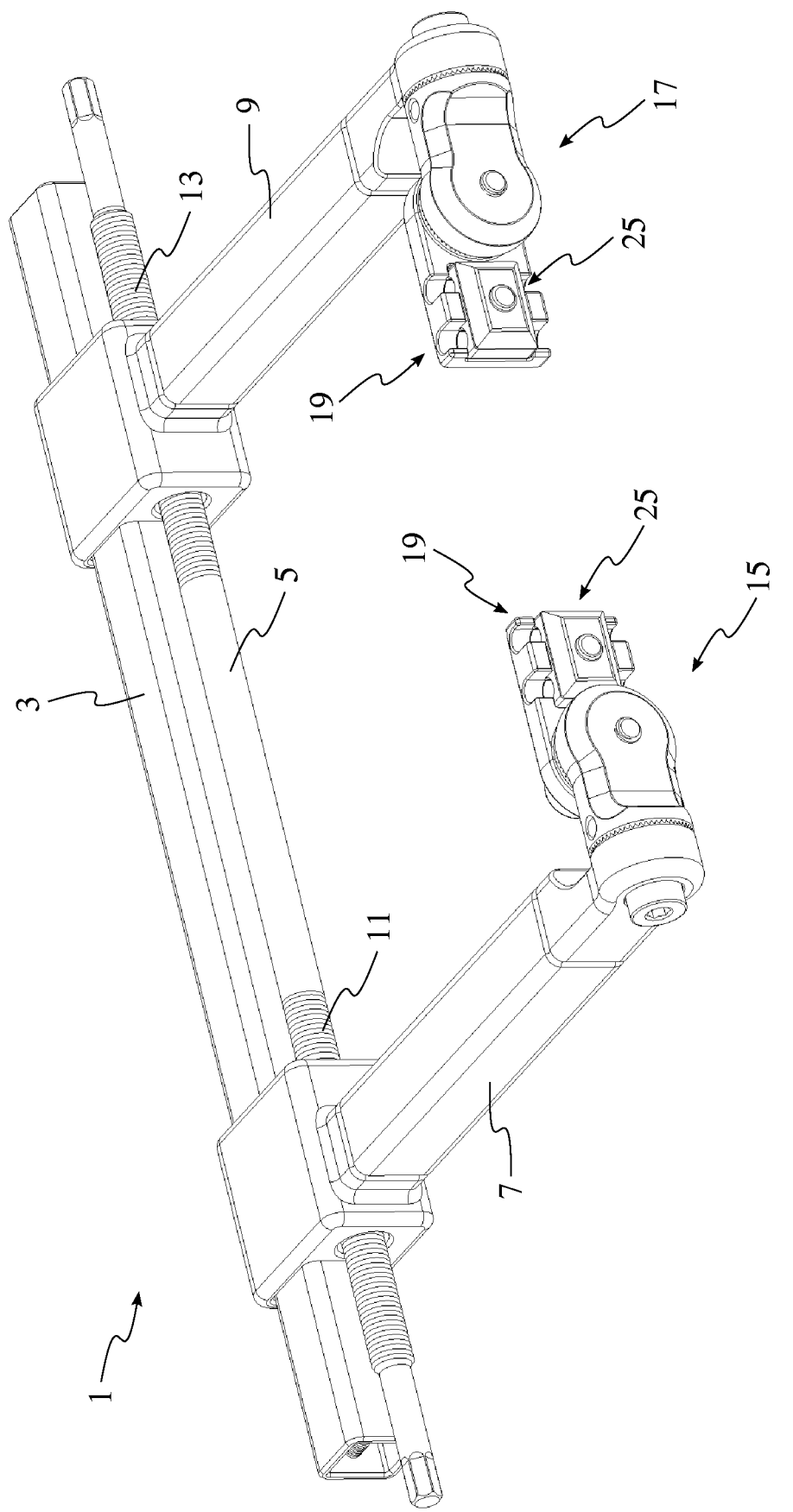
FIG. 1 is an isometric view of a distractor device according to one example of the present invention.
Figure 3:
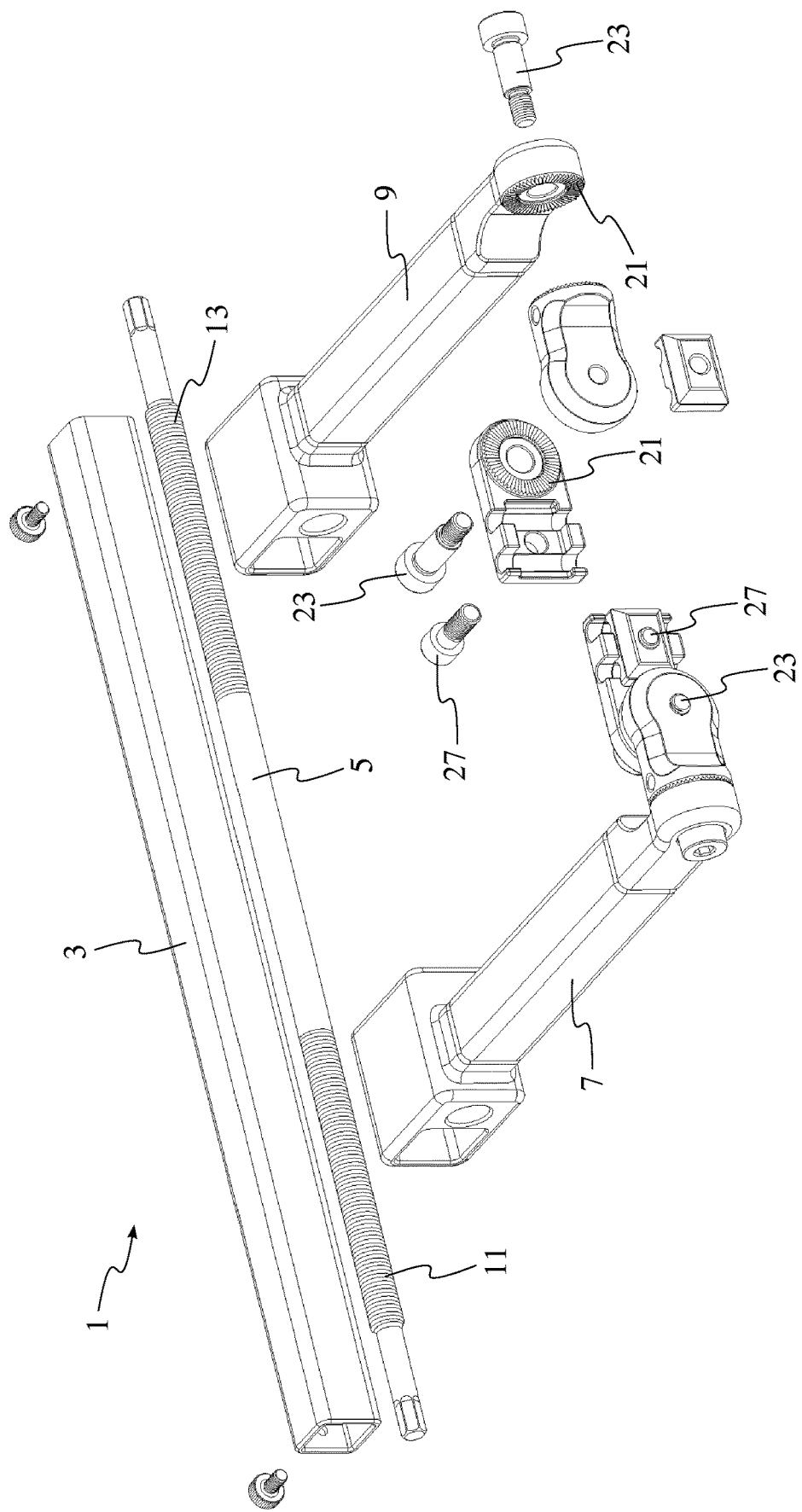
FIG. 3 is an exploded isometric view of the distractor device of FIG. 1.

An embodiment of the present invention will now be described in detail with reference to the attached figures. The invention will be described in the context of a distractor device used in hip distraction. However, the distractor device is not limited to be used in hip distractions. Indeed, the distractor device is not limited to use in the medical field, but may be used generally to pull two elements apart, such as the two halves of a ball joint of a vehicle's track rod end. Identical or corresponding functional and structural elements which appear in different drawings are assigned the same reference numerals.

The structure of the distractor device 1 according to an embodiment of the present invention is next explained in more detail with reference to FIGS. 1, 2a to 2e and 3. As can be seen, the distractor device 1 comprises a longitudinal guiding or runner element 3, and a longitudinal driving element 5, such as a threaded rod, which may be arranged substantially parallel to the guiding element 3 such that the threaded rod may rotate about a rotation axis substantially parallel to the longitudinal axis of the guiding element 3. The threaded rod may be arranged to be rotated by a ratchet tool for example, or by any other suitable tool. The ratchet tool may be two-sided, so that a first side can be used to rotate a socket attached to the ratchet mechanism in a first direction, while a second side can be used to rotate the socket in a second direction. In this way the tool does not need to include a ratchet lever or other mechanism for changing the rotation direction of the socket. This simple construction is advantageous when washing and/or sterilising the tool.

A first distractor arm 7 and a second distractor arm 9 are arranged to extend along a first, respectively second lateral axis from the guiding element 3. In this example the first and second lateral axes are substantially orthogonal to the longitudinal axis of the guiding element 3. The first and second distractor arms 7, 9 are captively displaceable along the guiding element 3, such that the first and second distractor arms 7, 9 are displaceable away from each other by rotating the threaded rod 5 in a first rotational direction, and towards each other by rotating the threaded rod 5 in a second rotational direction, the second rotational direction being opposite to the first rotational direction. The threaded rod 5 may comprise a first threaded drive section 11 engaging with a corresponding thread of the first distractor arm 7, and a second threaded section 13 engaging with a corresponding thread of the second distractor arm 9. The threaded engagement of the first threaded section 11 with the first arm 7 may be opposite to the threaded engagement of the second threaded section 13 with the second arm 9, such that the first and second arms 7, 9 always move in opposite directions along the longitudinal axis when the threaded rod 3 is rotated. The first threaded section may have a right-hand thread, and the second threaded section a left-hand thread.

Each of the first and second distractor arms 7, 9 may advantageously be provided in its distal region (the end of the arm which is not connected to the guiding element 3) with a fixation element or fixation head 15, 17 for securing the distal region to a first, respectively second bone of a joint to be distracted. The securing can be done by securing means such as bone screws, as explained later. The first and/or the second fixation element 15, 17 may be configured to be rotatable with a first and/or a second rotational degree of freedom with respect to its respective distractor arm. The first rotational degree of freedom is about a first fixation element axis substantially parallel to the longitudinal axis of the guiding element 3, for example, and the second rotational degree of freedom may be about a second fixation element axis substantially parallel to the longitudinal axis of the respective distractor arm 7, 9. It is to be noted that that, instead of being configured to be rotatable, the first and second fixation elements 15, 17 may be configured to be fixed with respect to the respective distractor arm 7, 9. Or they may have only one rotational degree of freedom. For example, when the distractor device 1 is used for hip distraction, the first rotational degree of freedom is sufficient.

The first and/or second fixation elements 15, 17 may further comprise holding means 19 for fixing one or more bone screws to the fixation element 15, 17. The holding means 19 may advantageously be configured to permit a rotational adjustment of the bone screw(s) with at least one further rotational degree of freedom with respect to the fixation element 15, 17. By arranging the rotational freedom of the components of the fixation element 15, 17 close to the bone screws, and therefore close to the bones, it is possible to achieve a highly effective transfer of distracting force from the distractor arms 7, 9 to the bones, and to permit a simple, robust construction of the main frame elements of the distractor 1, namely the guiding element 3 and the arms 7, 9. The holding means 19 may comprise a screw clamp 25 as explained later.

As better shown in FIGS. 2a to 2e and 3, the first and/or second degrees of rotational freedom may advantageously be provided by toothed or textured planar face-gears 21 or clutches, which can provide easy rotation when the opposing faces of the clutch are not pressed together, but which can be locked into the desired rotational position by forcing the faces together (eg by tightening a first clamping screw 23) to provide a very strong locked joint capable of transferring the large forces (eg 500 N) required during the distraction. The clutches 21 may be provided with markers, to indicate the angle of rotation of one face with respect to the opposing face. In this manner it easy for the operator to ensure that the two fixation elements 15, 17 are set at the same angles, for example. The toothed faces may be arranged so that the joint can be set in discrete angular steps of equal magnitude, where the magnitude of each rotational step is preferably between 1 to 12 degrees, or more preferably between 4 and 8 degrees. In this specific example, one rotational step is substantially 6 degrees. The bone screws may be clamped to the fixation element 15, 17 using the screw clamp 25. One screw clamp may be configured to accommodate one, two or more bone screws. As shown, in this example a second clamping screw 27 is provided for adjusting the screw clamp 25. A single second clamping screw may be used to clamp one, two or more bone screws. The first and second clamping screws 23, 27 can be designed so that they can be adjusted by the same tool that is used to rotate the driving element 5.

A distractor device 1 according to one embodiment of the present invention has been described above. The device 1 is easily washable and sterilisable; it has a strong construction, so that it can withstand large forces required in the distraction process; and it is light in weight, so that it is easy to manoeuvre and does not impose significant rotational forces on the bones being distracted due to its weight. The main elements of the distractor device 1, ie the guiding element 3, the driving element 5 and the arms 7, 9, can be made of aluminium alloy, steel alloy, other alloy or nanostructured ceramic materials, for example. The U-shape of the distractor device 1 is also designed to leave an opening between the distractor arms 7, 9 to leave the distracted joint clear for X-raying. The cross-section of the guiding element 3 was shown to be substantially square or rectangular. This has the additional advantage that the strength of the guiding element can be further increased, while preventing any undesired rotation of the distractor arms 7, 9 relative to each other. To reduce friction between the guiding element 3 and the distractor arms 7, 9, the guiding element may be provided with a solid lubricant surface, such as a graphite coating.

Figure 4:
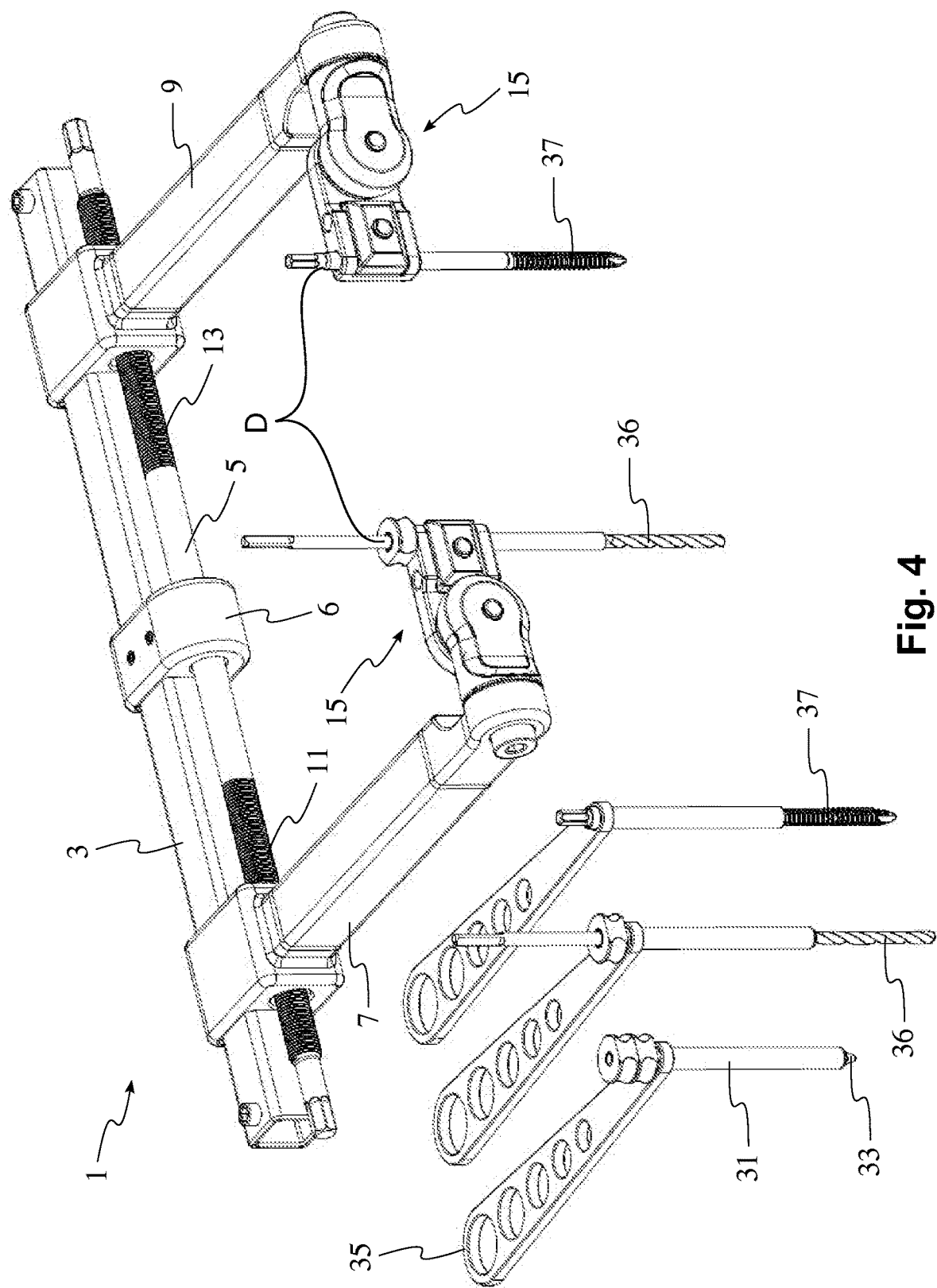
FIG. 4 is an isometric view of another example distractor device according to the invention, together with tools used in joint distraction.
Figure 5:
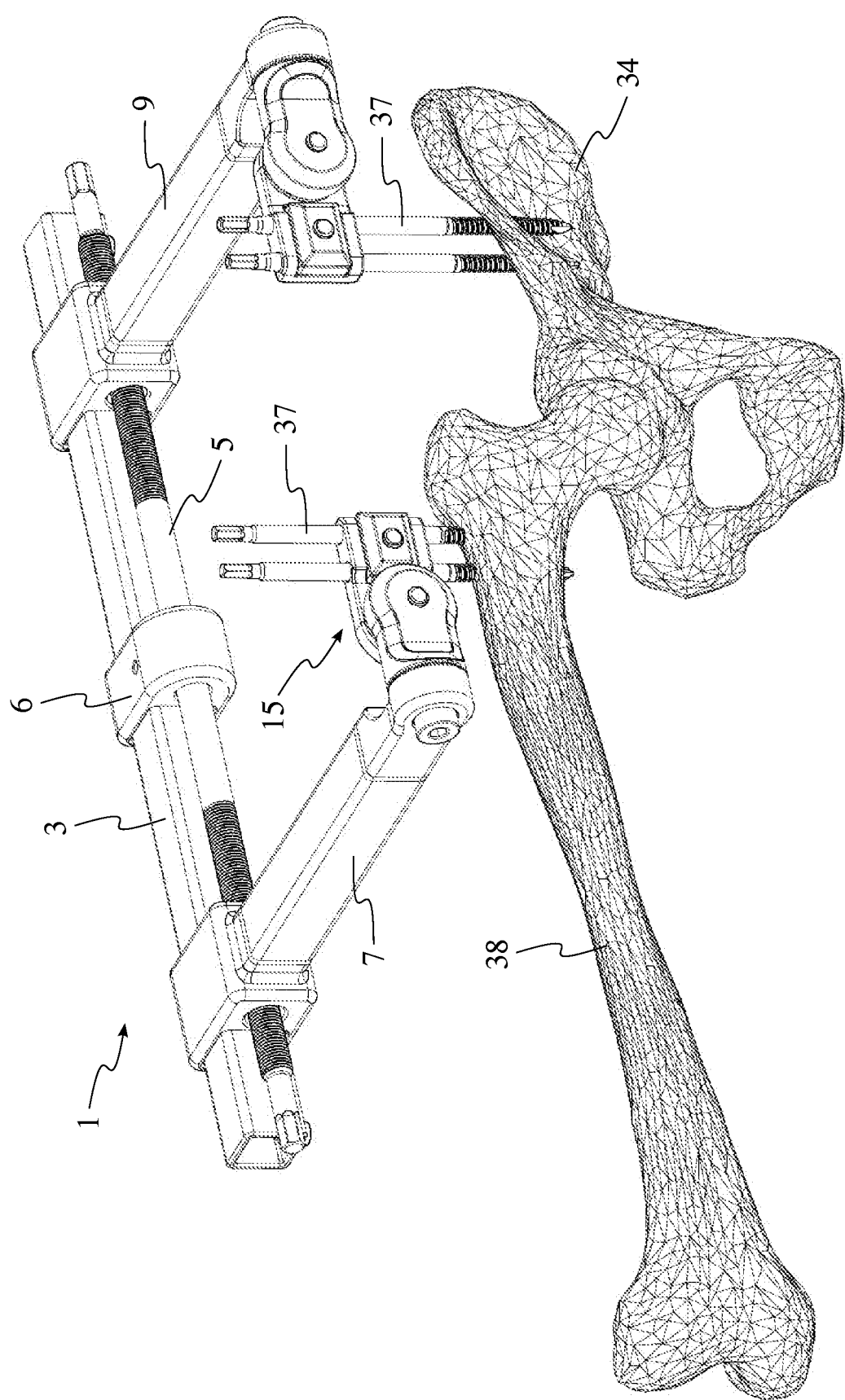
FIG. 5 is an isometric view of the distractor device of FIG. 4 when used in joint distraction.

Next, an exemplary method of operating the distractor device 1 is explained with reference to FIGS. 4 and 5 when used in hip distraction. It is to be noted that the distractor device 1 of FIGS. 4 and 5 shows an optional supporting element 6, which is configured around the guiding element 3 and has an opening for the driving element 5 to pass through it. The supporting element 6 may serve to support and/or stabilise the driving element 5 and thereby prevent it from buckling under the longitudinal compression load which is present in the driving element 5 when the distractor is in operation. In the method, once an incision is made on the patient's skin, a drill sleeve or guide 31 with a trocar 33 inside it is pushed through the flesh to reach a pelvic bone 34. The drill sleeve 31 is held in place with a handle 35 while the trocar 33 is withdrawn from the drill sleeve 31. The purpose of the drill sleeve is to protect the flesh during operation to provide a passage out for the drill waste. Next, a hole can be drilled by a drill 36 into the pelvic bone 34 so that the drilling is done through the drill sleeve 31. Then a dedicated bone screw 37, in this example a cortical hip screw, is screwed into the hole in the pelvic bone 34. Now the drill sleeve 31 can be removed. Other types of screws could be used instead, such as cancellous or cannulated screws. When the distractor device 1 is used for hip distraction, the screws 37 are made to sustain pressures preferably up to 1400 N/mm².

Next, the distractor device 1 is put in place, at least approximately. When used in hip distraction, the distance D as shown in FIG. 4 is typically in the range of 10 cm to 14 cm, and more specifically about 12 cm. The clamping screws 23, 27 may be adjusted if necessary. The bone screw 37 is now slightly clamped by the second fixation element 17. Another incision on the patient's skin is made above the thigh bone 38. The drill sleeve 31 with the trocar 33 inside are now pushed through the flesh to reach the thigh bone 38. The drill sleeve 31 may be hold in place by the first fixation element 15 as shown in FIG. 4. The trocar 33 is then removed to allow the drill 36 to pass though the drill sleeve 31. Now the drilling can be done through the drill sleeve 31. The remaining two drilling operations can be done in the same manner through the remaining two screw channels in the first and second fixation elements 15, 17.

Once all the four bone screws 37 have been screwed into the bones, the second clamping screws 27 can be tightened so that the fixation elements 15, 17 firmly clamp the clamping screws 37. Now the positions of the first and second fixation elements 15, 17 may be adjusted, so that the first and second fixation elements 15, 17 are preferably set at the same angles. The first and second distractor arms 7, 9 may be angled with respect to the first and second fixation elements. This angle may be for example +/−24 degrees or +/−36 degrees. Now the hip can be distracted by turning the drive element 5. In this manner both the first and second distractor arms 7, 9 are moved simultaneously and in opposite directions so that the distance between them is increased and thus the hip can be distracted. Once the arthroplasty or arthroscopy operation has been finished, the hip can be returned to its normal state by bringing the distractor arms 7, 9 into a position where no force is exerted on the bones. Again, the distractor arms 7, 9 are moved by turning the driving element 5, but in the opposite direction compared to a situation, where the hip distraction took place.

Figure 6:
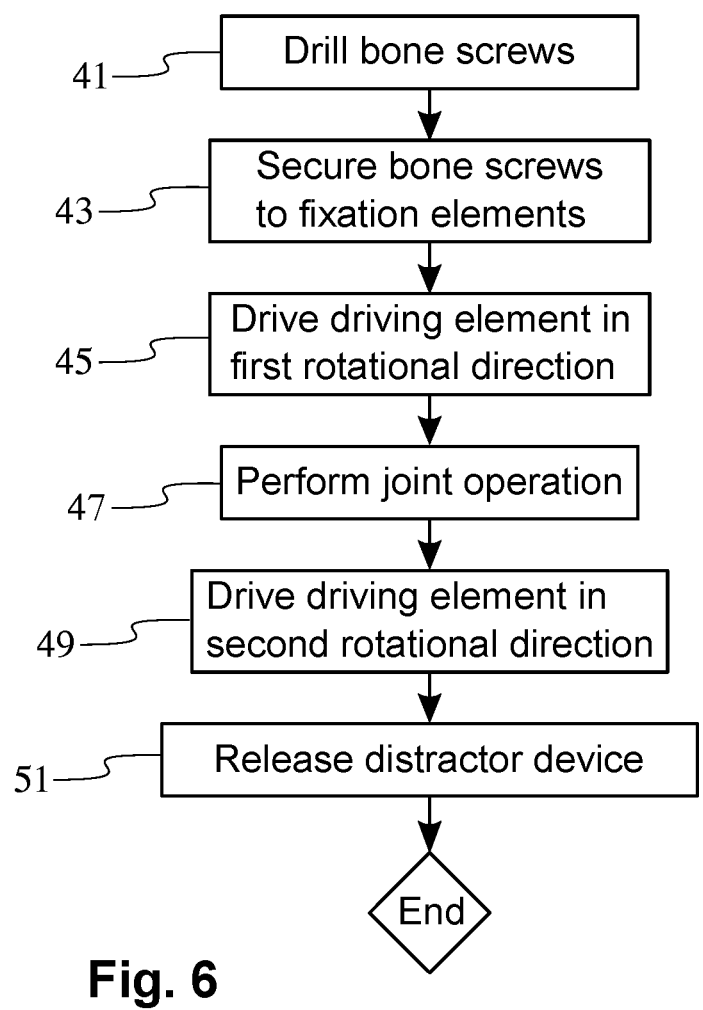
FIG. 6 is a flow chart summarising the method of operating the distractor device according to one example.

The above procedure can be summarised by the flow chart of FIG. 6. In step 41 the bone screws 37 are drilled into the bones as explained above in more detail. In step 43 the bone screws 37 are secured to the first and second fixations elements. In step 45 the driving element is rotated in the first rotational direction to displace the first and second distractor arms 7, 9 away from each other for distracting the joint. In step 47 an operation in the joint between the distracted bones is done. In step 49 the driving element is rotated in the second rotational direction to bring the distractor arms 7, 9 closer to each other for bringing the bones again to their initial position. In step 51 the distractor device 1 is released from the bone screws 37 and in step 53 the bone screws are removed from the bones.

Invasive hip distraction with the invention obviates the need for distraction on a traction table, so the complications experienced in many known methods can be avoided or at least minimised. Sufficient hip distraction implies traction forces of about 250 to 500 N. Once the suction seal of the joint is broken, the force needed diminishes significantly. However, on a traction table, much of the traction force is lost in needlessly distracting the knee (about 5 mm) and ankle joints (another 5 mm). Also, on a traction table, the femoral head (ie the highest part of the thigh bone 38) has a tendency to slide anteriorly and reduce the anterior joint space because of the acetabular anteversion. However most often, the lesions are in the anterior and superior regions and most surgeons prefer to internally rotate the lower extremity to avoid this anterior joint space narrowing on a traction table. Internal rotation moves the sciatic nerve anteriorly and thus puts it at risk if the surgeon chooses a posterolateral approach. Invasive hip distraction avoids this by allowing a controlled anterior to posterior traction vector in neutral rotation. A posterolateral approach is thus very safe without putting the sciatic nerve at risk.

The distractor device 1 according to the invention, once installed, may produce a traction force on the hip joint of 500 N, for example, without any unnecessary forces applied to other joints. This force is calculated in the elasticity of the dedicated cortical hip screws 37. Once this traction force is attained, the dedicated cortical hip screws 37 will be seen to start bending. The invention also permits a surgical intervention to be carried out without time pressure in order to attain the same degree of perfection as in open surgery. The results obtained are can therefore be as good as those of open surgery. Furthermore, the distractor device 1 allows the patient to lie on their side during the distraction operation and there is no need to raise patient's leg as in some known hip distraction methods.

The handle 35 may be designed so that it may approximately have a T shape so that the cross bar of the T shape would have two or more holes to allow the drill sleeve to pass through. The cross bar could have for example three equally distanced holes. The T-shaped handle could be used, together with the drill sleeve 31 and drill 36, to drill the holes into the bones. In this variant, the distractor device 1 would only be put in place once all the screws have been drilled into the bones.

While the invention has been illustrated and described in detail in the drawings and foregoing description, such illustration and description are to be considered illustrative or exemplary and not restrictive, the invention being not limited to the disclosed embodiment. Other embodiments and variants are understood, and can be achieved by those skilled in the art when carrying out the claimed invention, based on a study of the drawings, the disclosure and the appended claims.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used. Any reference signs in the claims should not be construed as limiting the scope of the invention.

The invention claimed is:

1. A joint distractor device comprising:
a longitudinal guiding element, and a longitudinal rotatable driving element arranged substantially parallel to the guiding element such that the driving element may rotate about a rotation axis substantially parallel to the longitudinal axis of the guiding element; and
a first distractor arm and a second distractor arm each threadedly connected to the driving element, the first distractor arm extending from the guiding element along a first lateral axis, and the second distractor arm extending from the guiding element along a second lateral axis, the first and second lateral axes being substantially orthogonal to the longitudinal axis of the guiding element, and the first and second distractor arms each being captively displaceable along the guiding element away from each other along the longitudinal axis by rotating the driving element in a first rotational direction, and captively displaceable along the guiding element towards each other along the longitudinal axis by rotating the driving element in a second rotational direction, the second rotational direction being opposite to the first rotational direction.

2. The distractor device according to claim 1, wherein the driving element is a threaded rod.

3. The distractor device according to claim 2, wherein the threaded rod comprises a first threaded section for engaging with a corresponding thread of the first distractor arm, and a second threaded section for engaging with a corresponding thread of the second distractor arm.

4. The distractor device according to claim 3, wherein the threaded engagement of the first threaded section with the first distractor arm is opposite to the threaded engagement of the second threaded section with the second distractor arm, such that the first and second distractor arms are arranged to move in opposite directions along the longitudinal axis when the threaded rod is rotated.

5. The distractor device according to claim 3, wherein the first threaded section has a right-hand thread, and the second threaded section has a left-hand thread.

6. The distractor device according to claim 1, wherein each of the first and second distractor arms comprises in its distal region a first fixation element and a second fixation element, respectively, for securing the distal region to a first bone and to a second bone, respectively, of a joint to be distracted.

7. The distractor device according to claim 6, wherein the first and second fixation elements are configured to be rotatable with a first rotational degree of freedom with respect to its respective distractor arm.

8. The distractor device according to claim 7, wherein the first rotational degree of freedom is about a first fixation element axis substantially parallel to the longitudinal axis of the guiding element.

9. The distractor device according to claim 7, wherein the first and second fixation elements are configured to be rotatable with a second rotational degree of freedom with respect to its respective distractor arm, the second rotational degree of freedom being different from the first rotational degree of freedom.

10. The distractor device according to claim 9, wherein the second rotational degree of freedom is about a second fixation element axis substantially orthogonal to the longitudinal axis of the guiding element.

11. The distractor device according to claim 6, wherein the first and second fixation elements comprise toothed or textured clutches to provide first and/or second degrees of rotational freedom, the clutches are arranged to provide rotation when opposing faces of the clutch are not pressed together, but which are arranged to be lockable into a desired rotational position by forcing the faces together.

12. The distractor device according to claim 11, wherein at least some of the clutches are provided with markers to indicate an angle of rotation of one face with respect to its opposing face.

13. The distractor device according to claim 6, wherein the first and second fixation elements comprise holding means for fixing one or more bone screws to the fixation elements.

14. The distractor device according to claim 13, wherein the holding means is configured to permit a rotational adjustment of the bone screw(s) with at least one further rotational degree of freedom with respect to the first and second fixation elements.

15. A method of operating the distractor device of claim 1, comprising:
  securing a first distal region of the first distractor arm to a first attachment element of a joint to be distracted and a second distal region of the second distractor arm to at least a second attachment element of the joint to be distracted; and
  rotating the driving element in a first rotational direction so as to displace the first and second distractor arms captively along the guiding element away from each other, thereby distracting the joint.

* * * * *